(12) United States Patent
Guenther et al.

(10) Patent No.: US 10,435,364 B2
(45) Date of Patent: Oct. 8, 2019

(54) COMPOUNDS FOR USE AS BROMODOMAIN INHIBITORS

(71) Applicant: Albert Ludwigs Universität Freiburg, Freiburg (DE)

(72) Inventors: Stefan Guenther, Freiburg (DE); Xavier Lucas, Dundee (GB); Manfred Jung, Gundelfingen (DE); Oliver Einsle, Freiburg (DE); Daniel Wohlwend, Karlsruhe (DE); Stefan Gerhardt, Gundelfingen (DE)

(73) Assignee: Albert Ludwigs Universität Freiburg, Freiburg (DE)

( * ) Notice: Subject to any disclaimer, the term of this patent is extended or adjusted under 35 U.S.C. 154(b) by 0 days.

(21) Appl. No.: 14/784,620

(22) PCT Filed: Apr. 15, 2014

(86) PCT No.: PCT/EP2014/057676
§ 371 (c)(1),
(2) Date: Oct. 15, 2015

(87) PCT Pub. No.: WO2014/170350
PCT Pub. Date: Oct. 23, 2014

(65) Prior Publication Data
US 2016/0068485 A1    Mar. 10, 2016

(30) Foreign Application Priority Data

Apr. 17, 2013  (EP) .................................... 13164209
Jan. 29, 2014  (EP) .................................... 14153141

(51) Int. Cl.
*C07D 207/34*  (2006.01)
*A61K 31/40*  (2006.01)

(52) U.S. Cl.
CPC ............ *C07D 207/34* (2013.01); *A61K 31/40* (2013.01)

(58) Field of Classification Search
CPC ................................. C07D 207/34; A61K 31/40
See application file for complete search history.

(56) References Cited

U.S. PATENT DOCUMENTS

| 7,034,049 | B1 | 4/2006 | Pevarello et al. |
| 2009/0005416 | A1 | 1/2009 | Munchhor et al. |
| 2010/0029615 | A1 | 2/2010 | Munchhof et al. |
| 2010/0048539 | A1* | 2/2010 | Chianelli ............ C07D 401/04 514/217.06 |
| 2010/0183712 | A1 | 7/2010 | Strobel et al. |
| 2012/0252139 | A1 | 10/2012 | Bamborough et al. |

FOREIGN PATENT DOCUMENTS

WO    WO2001012189    *  2/2001    ........... A61K 31/415

OTHER PUBLICATIONS

Chemical Abstract Registry No. 1370888-71-3, indexed in the Registry File on STN CAS Online, Apr. 29, 2012.*
Moffett, R. B. Central Nervous System Depressants. VIII. Pyrroles. Journal of Medicinal Chemistry, 1968, 11, 1251-1252.*
Ito et al., A medium-term rat liver bioassay for rapid in vivo detection of carcinogenic potential of chemicals. Cancer Science, 2003, 94, 3-8.*

(Continued)

*Primary Examiner* — Robert H Havlin
(74) *Attorney, Agent, or Firm* — The Marbury Law Group, PLLC

(57) ABSTRACT

A compound of formula (1), (1'), (1") or (1"') or a pharmaceutically acceptable salt thereof, for use in the treatment of diseases or conditions for which a bromodomain inhibitor is indicated.

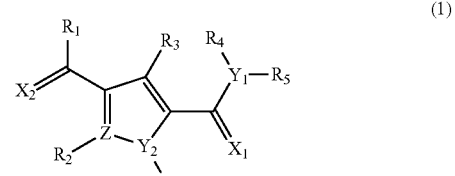

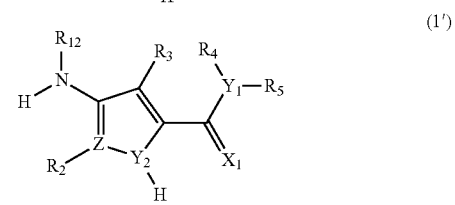

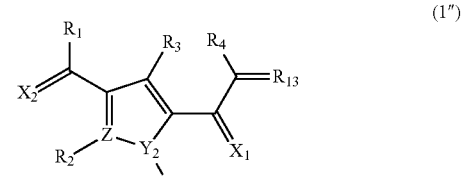

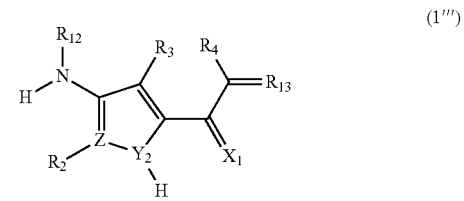

15 Claims, 3 Drawing Sheets

(56) References Cited

OTHER PUBLICATIONS

Hasvold et al. (Bioorganic & Medicinal Chemistry Letters 27 (2017) 2225-2233).*
Kubinyi (3D QSAR in Drug Design: Ligand-Protein Interactions and Molecular Similarity, vol. 2-3, Springer, 1998, 800 pages). pp. 243-244 provided.*
Wermuth, The Practice of Medicinal Chemsitry, 2d ed. (2003), 768 pages. Chs. 9-10 provided.*
Andreu et al. (Drug Discovery Today: Technologies, v. 19 (2016), p. 45-50).*
International search report received in connection with international application No. PCT/EP2014/057676; dated Sep. 12, 2014.
Written opinion received in connection with international application No. PCT/EP2014/057676; dated Sep. 12, 2014.
Lucas et al., "4-Acyl Pyrroles: Mimicking Acetylated Lysines in Histone Code Reading", Angewandte Chemie Int'l Edition, vol. 52(52), Dec. 23, 2013, pp. 14055-14059.
Wiley-VCH 2013 et al.., "Supporting Information: 4-Acyl Pyrroles: Mimicking Acetylated Lusines in Histone Code Reading", Angewandte Chemie, Nov. 24, 2013, pp. 1-29; retrieved from the internet: http://onlinelibrary.wiley.com/store/10.1002/anie.201307652/asset/supinfo/anie_201307652_sm_miscellaneous_information.pdf?v=1&s=b52f5b251109568cb5815246bba9489048d52e23.

* cited by examiner

COMPOUNDS FOR USE AS BROMODOMAIN INHIBITORS

The present invention relates to compounds for use as bromodomain inhibitors.

Bromodomains are epigenetic reader modules regulating gene transcription by recognizing acetyl-lysine modified histone tails.

The human genome encodes up to 61 different bromodomains (BRDs), present in transcriptional co-regulators and chromatin modifying enzymes including histone acetyltransferases (HATs) and the Bromodomain extra-terminal domain (BET) family. They are epigenetic mark 'readers' that specifically recognize ε-N-acetylated lysine residues ($K_{ac}$).

Drug molecules that target epigenetic mechanisms of gene regulation are attractive as they offer the perspective of modifying processes responsible for dysfunctional malignant states rather than just treating the results thereof.

Bromodomains are small distinct domains within proteins that bind to acetylated lysine residues commonly but not exclusively in the context of histones.

BRDs fold into an evolutionary conserved four antiparallel helix motif, linked by diverse loop regions of variable length (ZA and BC loops), which define the $K_{ac}$ binding site (Filippakopoulos et al. (2012), *Cell* 149(1), 214-231). In most BRDs, this site features an asparagine residue mainly responsible for substrate recognition (Owen D J, et al. (2000), The structural basis for the recognition of acetylated histone H4 by the bromodomain of histone acetyltransferase gcn5p, *The EMBO journal* 19(22):6141-6149; Umehara T, et al. (2010) Structural basis for acetylated histone H4 recognition by the human BRD2 bromodomain, *The Journal of biological chemistry* 285(10):7610-7618).

The biological function of BRDs and their potential as therapeutic targets have been thoroughly described in literature (Muller S, Filippakopoulos P, & Knapp S (2011), Bromodomains as therapeutic targets, *Expert reviews in molecular medicine* 13:e29; Prinjha R K, Witherington J, & Lee K (2012), Place your BETs: the therapeutic potential of bromodomains, *Trends in pharmacological sciences* 33(3): 146-153).

Research on the structural classification of bromodomains has revealed that the BET family of bromodomains has an overall highly targetable recognition site (Vidler L R, Brown N, Knapp S., Hoelder S (2012), Druggability analysis and structural classification of bromodomain acetyl-lysine binding sites, *Journal of medicinal chemistry* 55(17):7346-7359).

Members of the BET family, namely BRD2, BRD3, BRD4, and BRDT, modulate gene expression by recruiting transcriptional regulators to specific genomic locations. BRD4 and BRD2 have crucial roles in cell cycle control of mammalian cells. Along with BRD3, they are functionally linked to pathways important for cellular viability and cancer signalling and are co-regulators in obesity and inflammation. Specifically, BRD4 has been characterized as a key determinant in acute myeloid leukaemia, multiple myeloma, Burkitt's lymphoma, NUT midline carcinoma, colon cancer, and inflammatory disease. Because of its continued association with $K_{ac}$ in mitotic chromosomes, BRD4 has been postulated to be important for the maintenance of epigenetic memory.

Small molecules that inhibit bromodomains have potential as anti-inflammatory, antiviral, and anticancer agents. Anticancer activity is mainly due to down-regulation of the key oncogene c-MYC. Recently, cytotoxicity in LAC cells has been related to suppression of the oncogenic transcription factor FOSL1 and its targets.

WO2011/054851 discloses a process for the identification of bromodomain inhibitors.

WO2012/174487 describes bromodomain inhibitors of the general formula

WO2011/054553 describes a benzodiazepine bromodomain inhibitor having the formula which is also known as I-BET762 and which is in preclinical development as antagonist of the BET bromodomains BRD2, BRD3 and BRD4.

JP 2008/156311 discloses a benzimidazole derivative which is said to be a BRD2 bromodomain binding agent that has utility with respect to virus infection/proliferation.

WO 2009/084693 discloses thienotriazoleodiazepine derivatives having the general formula A molecule corresponding to this general formula, namely is known as (+)-JQ1 and is in pre-clinical development as bromodomain inhibitor.

Bamborough et al. (2012), *J. Med. Chem.* 55, 587-596, describe the optimization of phenylisoxazole sulphonamides of the general formula Hewings et al. (2011), *J. Med. Chem.* 54, 6761-6770 and Dawson et al. (2011), *Nature* 478 (7370), 529-533 disclose 3,5-dimethylisoxazole derivatives such as a compound known as I-BET151 which acts as a $K_{ac}$ mimic to inhibit bromodomains.

Zhao et al., Fragment based drug discovery of 2-thiazolidinones as inhibitors of the histone reader BRD4 bromodomain, *J. Med. Chem.*, DOI 10.1021/jm301793a (published online Mar. 26, 2013) disclose 2-thiazolidinones of general formula with compounds having a sulphonamide group wherein $R_4$ is an aryl or heteroaryl substituent selected from phenyl, thiophene or quinoline, as substituents $R_1$ and/or $R_2$ and/or $R_3$ showing the strongest inhibition of BRD4-BD1.

In this reference it is reported that fragments with very different chemical moieties appear to bind to a similar position in the BRD4-BD1 binding site. Hydrogen bonding to the conserved residue Asn140 of the BRD4 and indirect hydrogen bonding with Tyr97 is believed to be involved. Furthermore, apparently the solvent exposed area around Trp81, an entrance termed as the WPD shelf by Nicodeme et al. (2010), *Nature* 210, 1119-1123 is also involved in binding.

WO2012/150234 discloses bromodomain inhibitors of formula wherein P is a pyrazolyl or triazolyl ring.

WO97/003957 discloses distamycin derivatives of formula which are active as antitumor or antiviral agents.

As recognition of the acetyllysine of histone is a vital process of epigenetic regulations and as this process is mediated by bromodomains, developing novel bromodomain inhibitors is desirable to provide new approaches for pharmaceutically active ingredients.

Accordingly, it has been an object of the present invention to provide novel bromodomain inhibitors.

This object has been achieved with the compounds as defined in claim 1 for use in the treatment of diseases or conditions for which a bromodomain inhibitor is indicated.

Preferred embodiments of the present invention are set forth in the dependent claims and the detailed description hereinafter.

A brief description of the drawings is as follows.

The present invention relates to compounds of formula (1), (1'), (1") or (1''')

or a pharmaceutically acceptable salt thereof for use in the treatment of diseases or conditions for which a bromodomain inhibitor is indicated,
wherein $Y_1$ and $Y_2$, which may be the same or different at each occurrence, are CH, N or P, $X_1$ and $X_2$, which may be the same or different, are O or S, Z is C, S, C—$CR_6R_7$— or C—S—

$R_1$ is $C_1$-$C_8$ alkyl, $NHR_8$, $PHR_8$, $NH_2$, $PH_2$, a substituted or unsubstituted $C_1$-$C_8$-hydroxyalkyl group, or a substituted or unsubstituted $C_1$-$C_8$-alkoxy group, $R_2$ is hydrogen, a halogen atom, a cyano group or a thiocyanate or isothiocyanate group or a $C_1$-$C_8$ alkyl group, $R_3$ is hydrogen, $C_1$-$C_8$ alkyl. a substituted or unsubstituted $C_3$-$C_8$-carbocyclylgroup, a substituted or unsubstituted $C_3$-$C_8$-heterocarbocyclyl group comprising up to two heteroatoms selected from N, O and S, or a 5- or 6-membered aryl or heteroaryl group, $R_4$ and $R_5$, which may be the same or different at each occurrence, are hydrogen, a $C_1$-$C_8$ alkyl group, a $C_1$-$C_8$ alkoxy group, a $C_1$-$C_8$ hydroxyalkyl group, a substituted or unsubstituted $C_3$-$C_{14}$ cycloalkyl or heterocycloalkyl group or an unsubstituted or substituted $C_3$-$C_{14}$ aryl or heteroaryl group, which cycloalkyl, heterocycloalkyl, aryl or heteroaryl group may be bound to $Y_1$ directly or through a spacer of a $C_1$-$C_8$ alkylene group.

$R_6$ and $R_7$, which may be the same or different, are hydrogen or a $C_1$ to $C_8$ alkyl group and $R_8$ is hydrogen or a $C_1$ to $C_8$ alkyl group, $R_{12}$ is hydrogen, a $C_1$-$C_8$ alkyl group, a substituted or unsubstituted $C_3$-$C_8$-carbocyclylgroup, a substituted $C_1$-$C_8$ hydroxyalkyl group, a substituted or unsubstituted $C_1$-$C_8$ alkoxy group, a substituted or unsubstituted $C_3$-$C_8$-heterocarbocyclyl group comprising up to two heteroatoms selected from N, O and S, or a 5- or 6-membered aryl or heteroaryl group, and $R_{13}$ is O or S or as defined for $R_5$ provided that $R_5$ is bound to the molecule through a double bond.

The term $C_1$-$C_8$ alkyl group, when used herein, represents a linear or branched hydrocarbon group with 1 to 8 carbon atoms. Examples are methyl, ethyl, i-propyl, n-propyl, i-butyl, n-butyl and t-butyl, to name only a few representatives.

The term $C_1$-$C_8$ hydroxyalkyl group, when used herein, represents a linear or branched $C_1$-$C_8$-alkyl group in which one or more of the hydrogen atoms are replaced by a hydroxy group.

The term $C_1$ to $C_8$ alkoxy group, when used herein, represents a derivative of an alkyl group comprising at least one O—C bond. Representative examples are $OCH_3$, $OC_2H_5$, $OC_3H_7$ and $OC_4H_9$.

The term 5- or 6-membered substituted or unsubstituted carbocyclyl, heterocarbocyclyl, aryl, or heteroaryl group represents a five or six membered ring which may comprise carbon atoms and, optionally, one or more heteroatoms, preferably selected from O, S, N and P, more preferably from O, S and N, and particularly preferred from O and N. The ring may be saturated or it may carry double bonds, in particular it may be aromatic.

Preferred carbocyclyl rings are cyclopentyl and cyclohexyl, preferred heterocarbocyclyl groups are cyclopentyl and cyclohexyl groups in which one or more of the ring carbon atoms are replaced by a heteroatom selected from O, S, N and P as defined above.

Phenyl groups are representatives of six membered aromatic rings and 5- or six membered heteroaryl groups are preferably selected from the following ring systems.

2H-pyrrole    3H-pyrrole    1-substituted 1H-imidazole 2H-imidazole    4H-imidazole    1-substituted-1H-1,2,3-triazole All rings may be substituted or unsubstituted, i.e. one or more of the hydrogen atoms attached to the ring atoms in the unsubstituted representatives may be replaced by substituents consisting of halogen, alkyl, alkoxy, amino, cyano, alkenyl, alkynyl, arylalkyl, aryl, and heteroaryl groups.

The term substituted or unsubstituted $C_3$-$C_{14}$ cycloalkyl or heterocycloalkyl group or an unsubstituted or substituted $C_3$-$C_{14}$ aryl or heteroaryl group, when used herein, represents a ring system, which may be a fused ring system, comprising the indicated number of carbon atoms, and in which in the heterohydrocarbyl and heteroaryl groups one or more of the ring carbon atoms is replaced by a heteroatom selected from O, N, S and P, preferably O, N and S and most preferably N or O. All rings may be substituted or unsubstituted, i.e. one or more of the hydrogen atoms attached to the ring atoms in the unsubstituted representatives may be replaced by substituents consisting of halogen, alkyl, alkoxy, amino, cyano, alkenyl, alkynyl, arylalkyl, aryl and heteroaryl groups. Representative examples are cyclopropyl, cyclopentyl, cyclopentenyl, cyclopentadienyl, cyclohexyl, cycloheptyl, cyclooctyl, phenyl, napthyhyl and anthracenyl, which may all comprise one or more heteroatoms and one or more substituent groups as defined above.

Compounds of formula (1) and (1'), in particular compounds of formula (1) are especially preferred for use in accordance with the present invention.

A first preferred group of compounds for use in accordance with the present invention are compounds of formula (1), (1'), (1'') or (1''') wherein $Y_1$ or $Y_2$, more preferably $Y_1$ and $Y_2$ are N.

Particularly preferred are compounds of formulae (1), (1'), (1'') or (1''') wherein $Y_2$ is N.

In compounds of formulae (1') and (1''') $Y_1$ is preferably N.

Furthermore, preferably at least one of $X_1$ or $X_2$, preferably both $X_1$ and $X_2$ represent an oxygen atom.

In accordance with another preferred embodiment of the present invention Z is C or C—S—, preferably C. The respective compounds, in case $Y_2$ is N, are derivatives of pyrrole and isothiazole (i.e. in the latter case the sulphur atom in the ring is attached to the nitrogen atom).

$R_2$ is hydrogen, a halogen atom, a cyano group or a thiocyanate or isothiocyanate group or a $C_1$ to $C_8$ alkyl group. In certain cases $C_1$ to $C_6$ alkyl groups, halogen atoms or cyano groups have shown to be advantageous. Halogen atoms are selected from fluorine, chlorine, bromine and iodine atoms, with fluorine, chlorine and bromine being preferred. Methyl or ethyl are preferred representatives of alkyl groups, particularly preferred is a methyl group.

In accordance with another preferred embodiment $R_3$ is a $C_1$-$C_8$ alkyl group, preferably a $C_1$-$C_6$ alkyl group and particularly preferred $R_3$ is a methyl, ethyl, propyl, or isopropyl group. Other preferred examples for $R_3$ are $C_3$-$C_8$-cycloalkyl or $C_3$-$C_8$ heterocycloalkyl groups with up to two heteroatoms selected from N, O or S or 5- or 6-membered aryl rings, preferably phenyl, or 5- or 6-membered heteroaryl rings as defined above, with pyrrole, furan, imidazole, thiophene or thiophene as preferred examples. All ring systems may be substituted or unsubstituted with halogen, cyano, thiocyanate, isocyanate or $C_1$-$C_8$ alkyl groups, with halogen, in particular fluorine, chlorine or bromine and preferably chlorine being preferred. Halogen or cyano substituted phenyl or pyridine may be mentioned as preferred here.

In accordance with still another preferred embodiment of the present invention $R_4$ and/or $R_5$ are hydrogen or a substituted or unsubstituted $C_3$-$C_{14}$ aryl group, more preferably a substituted phenyl group.

In accordance with another embodiment, one of $R_4$ and $R_5$ is a hydrogen atom and the other substituent is a $C_1$-$C_8$ alkyl group (preferably methyl or ethyl) or a substituted or unsubstituted $C_3$-$C_{14}$ aryl group, more preferably a substituted phenyl group.

For some indications compounds in which $R_4$ and/or $R_5$ is a phenyl group bearing a sulphonamido substituent (which may be in o-, m- or p-position relative to the carbon atom bound to $Y_1$ with a substituent in m-position showing particularly good results in some cases) have shown to yield particularly good results and a particularly preferred example for $R_4$ and/or $R_5$ is represented by formula 2

(2)

wherein $R_9$ is halogen, OH, SH, $SR_6$, cyano, thiocyanato, isothiocyanato, $NR_6R_7$, a $C_1$-$C_8$ alkyl group, a $C_2$-$C_8$ alkylene group, a $C_2$-$C_8$ alkynyl group or a $C_1$ to $C_8$ alkoxy group, wherein $R_6$ and $R_7$ are as previously defined and n is an integer of from 0 to 4, preferably of from 1 to 3.

$R_{10}$ and $R_{11}$, which may be the same or different, are hydrogen, a $C_1$-$C_8$ alkyl group or a substituted or unsubstituted $C_3$-$C_{14}$ cycloalkyl group, heterocycloalkyl, aryl or heteroaryl group or wherein $R_{10}$ and $R_{11}$ may form together a cyclocarbyl, heterocyclocarbyl, aryl or heteroaryl ring, each with 3 to 14 carbon atoms.

Particularly preferred are compounds with $R_9$ being a hydroxy or methoxy group and $R_{10}$ and/or $R_{11}$ being a $C_1$-$C_4$ alkyl group, in particular a methyl or ethyl group or wherein $R_{10}$ and $R_{11}$ together form a ring system, preferably a $C_3$-$C_9$ cyclocarbyl group, especially preferably cyclopentyl, cyclohexyl or cycloheptyl.

In accordance with a further preferred embodiment one of $R_4$ and $R_5$ is hydrogen.

A first group of particularly preferred groups for use in accordance with the present invention are compounds of formula (3)

(3)

wherein $R_5$ has the meaning as described above.

A particularly preferred compound for use in accordance with the present invention is represented by formula (4)

(4)

which has shown to be particularly effective for the intended use.

In accordance with the present invention the compounds of formula (1), (1'), (1") or (1''') may be used in the form of their pharmaceutically acceptable salts. The skilled person is aware of pharmaceutically acceptable salts of compounds of formula (1), (1'), (1") or (1''') and will select the appropriate salt based on his professional experience and knowledge. Suitable pharmaceutically acceptable salts can include acid or base addition salts. For a review on suitable salts see Berge et al. (1977) J. Pharm. Sci. 66:1-19. Typically, pharmaceutical acceptable salts may be readily prepared by using a desired acid or base as appropriate. The resultant salt may precipitate from solution and be collected by filtration or may be recovered by evaporation of the solvent.

A pharmaceutically acceptable base addition salt can be formed by reaction of a compound of formula (1), (1'), (1") or (1''') with a suitable inorganic or organic base, optionally in a suitable solvent, to give the base addition salt which is usually isolated, for example by crystallization and filtration. Pharmaceutically acceptable base salts include ammonium salts, alkali metal salts, alkaline earth metal salts and salts with organic basis, in particular salt with primary, secondary and tertiary amines, e.g. isopropyl amine, diethylamine, ethanolamine, trimethylamine and dicyclohexylamine.

The pharmaceutically acceptable acid addition salt can be formed by reaction of a compound of formula (1), (1'), (1") or (1''') with a suitable inorganic or organic acid, in a suitable solvent such as an organic solvent, to give the product which is usually isolated, for example, by crystallization and filtration. Pharmaceutically acceptable acid addition salts of a compound of formula (1), (1'), (1") or (1''') can comprise or be, for example, a nitrate, sulphate, hydrobromide, hydrochloride, phosphate, maleate, acetate, propionate, fumarate, citrate, tartrate, salicylate, aspartate, succinate, benzoate, p-toluenesulphonate, methanesulphonate, naphthalenesulphonate, ethanesulphonate or hexanoate salt.

In accordance with the present invention the pharmaceutically acceptable salts include all possible stoichiometric and non-stoichiometric forms of the salts of the compounds of formula (1), (1'), (1") or (1''').

The compounds of formula (1), (1'), (1") or (1''') form complexes with solvents in which they are reacted or from which they are precipitated or crystallized, which complexes are generally referred to as solvates. In accordance with the present invention all possible stoichiometric and non-stoichiometric forms of the solvates of the compounds of formula (1) or (1') are included.

The present invention also encompasses all prodrugs of the compounds of formula (1), (1'), (1") or (1''') and pharmaceutically acceptable salts thereof, which upon administration to the recipient are capable of providing (directly or indirectly) a compound of formula (1), (1'), (1") or (1''') or a pharmaceutically acceptable salt thereof or an active metabolite or acceptable salt thereof. In this regard, reference is made to Burger's Medicinal Chemistry and drug discovery, 5th Ed., Vol. 1, Principles and Practice, to which reference is made here for further details.

The compounds of formula (1), (1'), (1") or (1''') may be in crystalline or amorphous form. Furthermore, some of the crystalline forms may exist in different morphological conformations, which are included within the scope of the present invention. Different morphological forms (polymorphic forms) of the compounds of formula (1), (1'), (1") or (1''') can be characterized and different analytical techniques are known to the person skilled in the art so that no further details are necessary here.

The compounds of formula (1), (1'), (1") or (1''') may also exist in one of several tautomeric forms and in accordance with the present invention individual tautomers or mixtures thereof are encompassed.

The compounds of formula (1), (1'), (1") or (1''') or their pharmaceutically acceptable salts are provided for use in the treatment of diseases or conditions for which a bromodomain inhibitor is indicated.

Bromodomain inhibitors are believed to be useful in the treatment of a variety of diseases or conditions related to systemic or tissue inflammation, inflammatory responses to infection or hypoxia, cellular activation and proliferation, lipid metabolism, fibrosis and in the prevention and treatment of viral infections.

Bromodomain inhibitors may thus be useful in the treatment of a great variety of chronic autoimmune and inflammatory conditions such as rheumatoid arthritis, osteoarthritis, acute gout, psoriasis, systemic lupus erythematosus, multiple sclerosis, inflammatory bowel disease, asthma, chronic obstructive airways disease, pneumonitis, myocarditis, pericarditis, myositys, eczema, dermatitis, alopecia, vitiligo, bullous skin diseases, nephritis, vasculitis, atherosclerosis, Alzheimer's disease, depression, retinitis, uveitis, scleitis, hepatitis, pancreatitis, primary biliary cirrhosis, sclerosis, cholangitis, Addison's disease, hypophysitis, thyroiditis, type I diabetes and acute rejection of transplanted organs.

The compounds in accordance with formula (1), (1'), (1") or (1''') for use in diseases or conditions for which a bromodomain inhibitor is indicated may also be useful in the prevention or treatment of diseases or conditions which involve inflammatory responses to infections with bacteria, viruses, fungi, parasites or the like, such as sepsis, sepsis syndrome, septic shock, endotoxemia, systemic inflammatory response syndrome (SIRS), multi-organ dysfunction syndrome, toxic shock syndrome, acute lung injury, adult respiratory distress syndrome, acute renal failure, fulminant hepatitis, burns, acute pancreatitis, post-surgical syndromes, sarcoidosis, Herxheimer reactions, encephalitis, myelitis, meningitis, malaria, and SIRS associated with viral infections such as influenza, herpes zoster, herpes simplex, and coronavirus.

The compounds of formula (1), (1'), (1") or (1''') may also be used in the treatment of disorders of the lipid metabolism while the regulation of APO-A1 such as hypercholesterolemia, atherosclerosis, and Alzheimer's disease.

Furthermore, the compounds of formula (1), (1'), (1") or (1''') may be used in the prevention or treatment of conditions associated with ischemia-reperfusion injury such as myocardial infarction, cerebrovascular ischemia (stroke), acute coronary syndromes, renal reperfusion injury, organ transplantation, coronary artery bypass grafting, cardiopulmonary bypass procedures and pulmonary, renal, hepatic, gastro-intestinal or peripheral limb embolism.

Bromodomain inhibitors may further be useful in the treatment of fibrotic conditions such as idiopathic pulmonary fibrosis, renal fibrosis, post-operative stricture, keloid formation, scleroderma and cardiac fibrosis.

A further indication for bromodomain inhibitors is the prevention and treatment of viral infections such as herpes virus, human papilloma virus, adenovirus, poxvirus and other DNA viruses.

The compounds of formula (1), (1'), (1") or (1''') are useful in the treatment of cancer, including but not limited to types of cancer included in the NCI60 panel, such as bladder cancer, brain cancer, breast cancer, cervical carcinoma, colorectal cancer, oesophageal cancer, gastric cancer, head and neck cancer, leukaemia, lymphoma, NSCLC cancer (non-small cell lung carcinoma), ovarian cancer, pancreatic cancer, sarcoma, SCLC cancer (small cell lung cancer), melanoma, renal cancer, prostate cancer and hepatocellular carcinoma. including haematological (such as leukaemia), epithelial including lung, breast and colon carcinomas, midline carcinomas, mesenchyme, hepatic, renal and neurological tumours.

Preferred uses of the compounds of formula (1), (1'), (1") or (1''') are the treatment of chronic autoimmune or inflammatory conditions, cancer or viral diseases.

The compounds of formula (1), (1'), (1") or (1''') can also be preferably used for the inhibition of proliferation of leukaemia cells or for the treatment of a disease or condition which is obesity or a kidney malfunction, in particular the compounds of formulae (3) and (4) have shown good efficiency in the inhibition of proliferation of leukaemia cells.

Furthermore, the compounds of formula (1), (1'), (1") or (1''') could also be effective as male contraceptives.

Compounds of formula (1), (1'), (1") or (1''') can also be used in the treatment of diseases or conditions related to bromodomains CREBBP and EP300. By way of example, acute myeloid leukaemia, acute lymphoblastic leukaemia, non-Hodgkin lymphoma, prostate cancer and spinal and bulbar muscular atrophy may be mentioned in this regard.

In the course of the studies leading to the present invention it has been recognized that the compounds of formula (1), (1'), (1") or (1''') in particular are effective in inhibiting the bromodomains of the BET family, including BRD2-BD1, BRD2-BD2, BRD3-BD1, BRD3-BD2, BRD4-BD1, BRD4-BD2, BRDT-BD1 and BRDT-BD2 as well as the bromodomains CREBBP and EP300, with a particularly good effect in the inhibition of the mentioned bromodomains of the BET family. In some cases, particularly good results were obtained in the inhibition of bromodomains BRD2-BD1, BDRD3-BD1 and BRD3-BD2 whereas in other cases efficient inhibition of BRD4-BD1 was observed.

A similar behaviour was observed for the compounds of formula (3), in particular where $R_5$ is an alkyl group. These compounds share a core with the compound of formula (4) but lack the sulphonamide substituent.

In accordance with the present invention, the compounds of formula (1), (1'), (1") or (1''') as well as their pharmaceutically acceptable salts may be administered as such or may be presented as active ingredients in a pharmaceutical composition.

Accordingly, a further embodiment of the present invention relates to a pharmaceutical composition comprising at least one compound of formula (1), (1'), (1") or (1''') or a pharmaceutically acceptable salt thereof for use in the treatment of diseases or conditions for which a bromodomain inhibitor is indicated and one or more pharmaceutically acceptable carriers, diluents or excipients.

The carriers, diluents or excipients used in pharmaceutical compositions must be acceptable in the sense of being compatible with the other ingredients of the composition and not detrimental to the recipient.

Such pharmaceutical compositions may be obtained by mixing a compound of formula (1), (1'), (1") or (1''') or a pharmaceutically acceptable salt thereof, with one or more pharmaceutically acceptable carriers, diluents or excipients.

Since the compounds and pharmaceutically acceptable salts thereof are intended for use in pharmaceutical compositions it is apparent that they are preferably provided in substantially pure form, i.e. with a degree of impurities as low as possible. Preferably the purity is at least 60%, more preferably at least 75% and most preferably at least 98% (in each case percent by weight).

Pharmaceutical compositions may be presented in unit dose forms containing a predetermined amount of active ingredient per unit dose. Preferred unit dosage compositions are those containing a daily dose or sub-dose, or an appropriate fraction thereof, of an active ingredient. Such unit doses may therefore be administered more than once a day. Preferred unit dosage compositions are those containing a daily dose or sub-dose as recited above.

The pharmaceutical compositions may be adapted for administration by any appropriate route, for example by the oral, rectal, inhalation, intranasal, topical, vaginal or parenteral route.

The skilled person will select the appropriate administration route based on the conditions of the specific application. The manufacture of the appropriate administration forms is known to the skilled person so that no further details are necessary here.

When desired or necessary, suitable binders, glidants, lubricants, sweetening agents, flavours, disintegrating agents and colouring agents can be included in the pharmaceutical composition. The skilled person will select the appropriate additives based on his professional experience and in adaptation to the specific application.

The pharmaceutical compositions in accordance with the present invention may comprise more than one active ingredient, e.g. more than one compound of formula (1), (1'), (1") or (1''') or a pharmaceutically acceptable salt thereof or a combination of a compound of formula (1), (1'), (1") or (1''') with other active ingredients or their pharmaceutically acceptable salts.

In particular combinations of bromodomain inhibitors of formula (1), (1'), (1") or (1''') and histone deacetylase inhibitors (HDAC inhibitors) provide a very interesting property spectrum and combination of efficiencies.

Various HDAC inhibitors useful to be combined with the compounds of formula (1), (1'), (1") or (1''') have been investigated and described in the literature and are known to the skilled person.

Vorinostat and Romidepsin have been approved by the US FDA for cutaneous T-cell lymphoma.

Panobinostat, valproic acid and belinostat are in phase III clinical trials for various types of cancer.

Mocetinostat, Abexinostat, Entinostat, Resminostat, Givinostat, Qusinostat and SB 939 are in phase II clinical trials.

CUDC-101, AR-42, ACY-1215, Kevetrin, Trichostatin A are in early stage development as HDAC inhibitors.

All the aforementioned HDAC inhibitors can principally be combined with the compounds of formula (1), (1'), (1") or (1''') in accordance with the present invention to obtain pharmaceutical compositions.

The compounds of formula (1), (1'), (1") or (1''') for use in accordance with the present invention present a novel class of interesting active molecules in the epigenetic field and in particular may be considered as a representative of a new class of bromodomain inhibitors of the BET family featuring a 4-acyl pyrrole moiety.

Certain compounds of formula (1) are commercially available, i.e. from Enamine Ltd.

The skilled person is aware of suitable methods for the synthesis of compounds of formula (1), (1'), (1") or (1''') so that there is no further description necessary here.

The compounds of formula (1), (1'), (1") or (1''') or a pharmaceutically acceptable salt thereof may be used in the manufacture of a medicament for the treatment of diseases or conditions for which a bromodomain inhibitor is indicated. In other embodiments, there is provided the use of a compound of formula (1), (1'), (1") or (1''') or a pharmaceutically acceptable salt thereof in the manufacture of a medicament for the treatment of a chronic autoimmune and/or inflammatory condition or in the treatment of cancer.

In a further embodiment there is provided a method for treatment of a disease or condition, for which a bromodomain inhibitor is indicated, in a subject in need thereof which comprises administering a therapeutically effective amount of a compound of formula (1), (1'), (1") or (1''') or a pharmaceutically acceptable salt thereof.

In one embodiment the subject in need of treatment is a mammal.

The term effective amount means an amount of a drug or pharmaceutical agent that will elicit the biological or medical response of a tissue, system, animal or human that is being sought, for instance by a researcher or a clinician. Furthermore, the term therapeutically effective amount means any amount which, as compared to a corresponding subject which has not received such amount, results in improved treatment, healing, prevention or amelioration of a disease, disorder, or side effect, or a decrease in the rate of advancement of a disease or disorder. The term also includes within its scope amounts effective to enhance normal physiological function.

The following examples represent embodiments of the present invention. The skilled person will easily recognize that he can modify the structure of the compounds in the working examples in an appropriate manner.

EXAMPLE 1

The compound of formula (4) and the compound of formula (3) with $R_5$ being methyl which were studied in the working examples were obtained from Enamine Ltd (compounds of formulae (3) and (4)) and InterChim Ltd. (compound of formula (4)).

Protein Preparation, Crystallization and Structure Determination

BRD4-BD1 was expressed and purified as described previously (Filippakopoulos et al, (2012), *Cell* 149(1): 241-231) with the exception of the final buffer for crystallization and ITC analysis (20 mM Hepes/NaOH pH 7.5, 150 mM NaCl). Crystals were grown in the presence of 3.5 M Na-Formate (pH 7.5) at a protein concentration of 10 mg/ml and a ligand concentration of 2 mM added directly to the protein prior to crystallization from a 100 mM stock solution in DMSO. Data were collected at 100K using either a Rigaku HF-007 rotating anode X-ray generator equipped with VariMaxHF optics and a Saturn944 CCD detector or a mar345 image plate respectively at $\lambda=1.54179$ Å or at the PXI beamline at the Swiss Light Source at $\lambda=1.000$ Å with a Pilatus detector. Data processing and reduction was done with iMOSFLM (Leslie AGW PH (2007), Evolving Methods for Macromolecular Crystallography 245, 41.51), POINTLESS, and SCALA (Kabsch W (2010) Xds. i Acta crystallographica. Section D, Biological crystallography 66(Pt 2):125-132; Bruker (2008) SADABS, SAINT and XPREP (Bruker AXS Inc., Madison, Wis., USA); Collaborative Computational Project N (1994) The CCP4 suite: programs for protein crystallography, *Acta crystallographica, Section D, Biological crystallography* 50(Pt 5):760-763), or with XDS, XSCALE, XDSCONV (Evans P (2006), Scaling and assessment of data quality, *Acta crystallographica, Section D, Biological crystallography* 62(Pt 1):72-82), and XPREP (Evans P R (2011), An introduction to data reduction: space-group determination, scaling and intensity statistics, *Acta crystallographica, Section D, Biological crystallography* 67(Pt 4):282-292).

BRD4•ligand complexes crystallized in space group $P2_12_12_1$. The structures were solved by molecular replacement with PHASER (McCoy A J, et al. (2007), Phaser crystallographic software, *Journal of applied crystallography* 40(Pt 4):658-674) with apoBRD4 as search model (internal data) yielding one molecule per asymmetric unit. Compounds were modelled into 2Fo-Fc electron density maps using AFITT-CL (version 2.1.0, OpenEye Scientific Software, Inc., Santa Fe, N. Mex., USA.) Model building and real space refinement was done with COOT (Murshudov G N, Vagin A A, & Dodson E J (1997), Refinement of macromolecular structures by the maximum-likelihood method, *Acta crystallographica. Section D, Biological crystallography* 53(Pt 3):240-255) reciprocal space refinement against the calculated data was done with Refmac5, as implemented in the CCP4 suite (Murshudov G N, et al. (2011), REFMAC5 for the refinement of macromolecular crystal structures, *Acta crystallographica. Section D, Biological crystallography* 67(Pt 4):355-367; Vaguine A A, Richelle J, & Wodak S J (1999), SFCHECK: a unified set of procedures for evaluating the quality of macromolecular structure-factor data and their agreement with the atomic model, *Acta crystallographica, Section D, Biological crystallography* 55(Pt 1):191-205). Final structure validation was done with procheck/sfcheck (Wlodek S, Skillman A G, & Nicholls A (2006), Automated ligand placement and refinement with a combined force field and shape potential, *Acta crystallographica, Section D, Biological crystallography* 62(Pt 7):741-749).

Isothermal Titration Calorimetry

ITC experiments for the determination of the dissociation constant $K_d$ were done with a Microcal VP-ITC microcalorimeter (GE Healthcare) at 25° C. using ligand concentrations between 10 and 50 µM in the sample cell and BRD4 concentrations between 120 and 600 µM in the injection syringe. Data were obtained in discrete titration experiments with an injection volume of 12 µl per injection. Subsequently, the heats per injection were calculated as integrals and after normalization against the molar concentrations plotted against the molar ratio as implemented in Microcal Origin. Finally, data were fitted according to a single set of sites binding model with $$Q = nM_t \times \Delta HV_0 \times \frac{1}{2} \times \left(1 + \frac{X_t}{nM_t} + \frac{1}{nKM_t} - \sqrt{\left(1 + \frac{X_t}{nM_t} + \frac{1}{nKM_t}\right)^2 - \frac{4X_t}{nM_t}}\right) \quad (1)$$

as function to calculate the overall sum of heat of the titration and with $$\Delta Q(i) = Q(i) + \frac{dV_i}{V_0} \times \left(\frac{Q(i) + Q(i-1)}{2}\right) - Q(i-1) \quad (2)$$

(According to Microcal's manual "ITC Data Analysis in Origin" (September 1998)) as function describing the sum of heat of each individual injection. A correction term was included to compensate for displacement of volume of the sample cell in the course of subsequent injections according to the manufacturer's manual "ITC Data Analysis in Origin" (Microcal).

The dissociation constant $K_d$ is commonly used to describe the affinity between a ligand L and a protein, i.e. how tightly a ligand binds to a particular protein. The dissociation constant has molar units which correspond to the concentration of ligand at which the binding site on a particular protein is half occupied, i.e. the concentration of the ligand at which the concentration of protein with ligand bound equals the concentration of protein with no ligand bound. The smaller the dissociation constant, the higher the affinity between ligand and protein.

For the compound of formula (4) the dissociation constant $K_d$ for BRD4-BD1 was determined to be 0.3 µM whereas the respective value for the compound of formula (3) with $R_5$ being methyl was 20 µM. The compound of formula (4) thus showed an improved affinity compared to the compound of formula (3) with $R_5$ being methyl.

The concentration required to reduce the population of a culture of HL-60 cells by 50% ($GI_{50}$) was 14 µM for the compound of formula (4).

Bromodomain Profiling

Bromodomain profiling was carried out on the basis of BROMOscan™. This platform accounted for the indirect determination of the dissociation constants between 19 bromodomains and the compound of formula (4), by binding competition against a reference immobilized ligand.

The overall structure of the complex of the compound of formula (4) and BRD4-BD1 revealed the already well-characterized bromodomain fold with a bundle of four α-helices, interconnected by three loops of different length. The termini of the helices bundle are flanked by elongational loops, which tightly pack against the protein core producing a compact and rather rigid structure.

The compound of formula (4) is bound in a pocket located at the end of the longitudinal axis running through the helix bundle which points towards the N-terminus. Consequently, it occupies the same pocket as the native $K_{ac}$ substrate.

Moreover, it mimics the $K_{ac}$ interaction with BRD4-BD1 by positioning the 4-acyl substitution in the pyrrole ring toward the highly conserved Asn140, thus engaging in hydrogen bond interactions with Asn140 and the equally conserved water molecule that bridges to the conserved Tyr97. The pyrrole ring is located deep in the recognition pocket, and complements the hydrophobic pocket defined by the four conserved waters with a 5-methyl substitution. The surface complementarity between the ligand and the recognition pocket is further achieved by the 3-ethyl substitution in the pyrrole ring. The presence of the heteroatom in the core of the compound of formula (4) allows for a key hydrogen-bond donor interaction with the proline's backbone in position 82. Such interaction has not been described previously, and may have an important role in fixating the compound in the recognition site.

Apart from this major determinant of ligand recognition by BRD4-BD1, the compound of formula (4) also explores another patch of interactions.

The phenylsulphonamide moiety is placed along the ZA channel, such that a T-shaped CH-π interaction with Trp81 is established, whereby a perfect orthogonal orientation of both aromatic systems is created withTrp81 directly pointing towards the centre of the phenyl moiety of the compound of formula (4). Such interactions have already been reported in other drug-protein interactions. In addition, Leu92 serves as lid from the opposing side and together with Trp81 it forms a special configuration which will be referred to hereinafter as WL trap.

The compound of formula (3) with $R_5$ being a methyl group represents a shortened fragment of the compound of formula (4) lacking the phenylsulphonamide extension, and consequently, it perfectly fits into the site around Asn140 and the conserved waters; yet it fails to establish the interaction with the WL trap.

It appears that the WL trap adds to the specificity of the binding. Notably, both Trp81 and Leu92 are conserved within the BET bromodomain family.

The target selectivity of the compound of formula (4) within the human BRD family was assessed by means of BROMOscan™. The binding of the compound to at least one representative protein of each BRD family was assessed. The results are summarized in FIG. 1.

Figure 1:
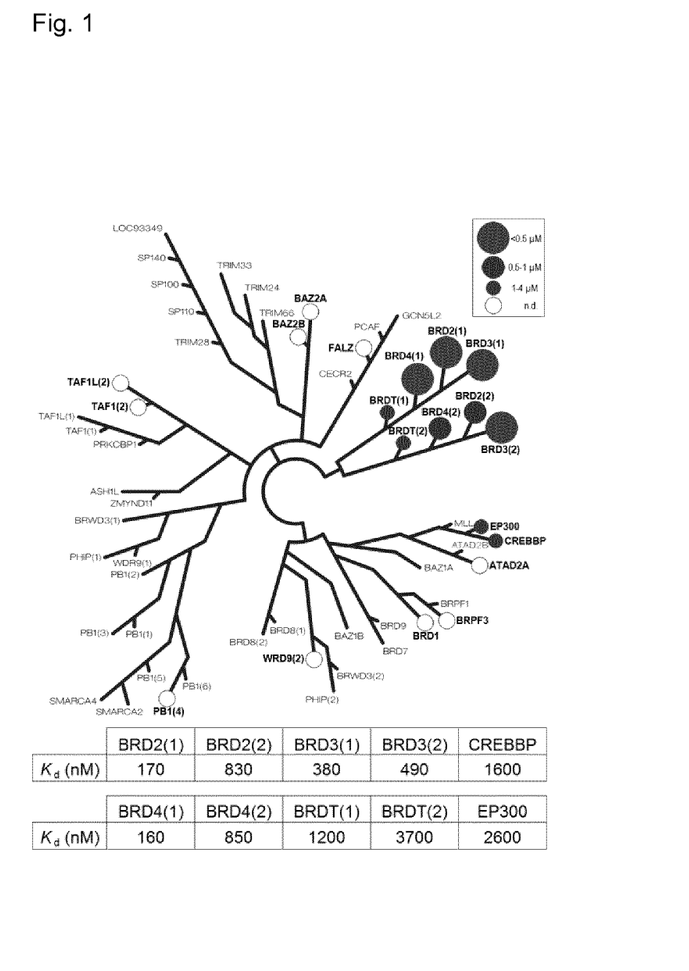
FIG. 1 shows the selectivity profile of a compound of formula (4) within the human BRD family.

FIG. 1 shows the selectivity profile of the compound of formula (4) within the human BRD family. Sphere size and colour indicate the binding affinity of the compound of formula (4) to the specific BRDs, as observed in the BROMOscan™ assay. Additionally, binding to PB1-BD4 was assessed by local ITC measurements. The dissociation constant ($K_d$) corresponding to each BRD in complex with the compound of formula (4) is indicated. The sequence similarity-based phylogenetic tree of the BRD family was extracted from the profiling visualization tool TREEspot™ and reproduced under permission of DiscoveRx Corp. The reproducible value of the dissociation constant ($K_d$) of the compound of formula (4) in complex with BRD4-BD1 was shown to be 0.16 µM (n=2) in terms of this assay, in close agreement with the 0.3 µM observed by ITC measurements (n=5). P In the BROMOscan™ assay, the compound of formula (4) was found to bind specifically to the BET bromodomain family. It exhibited affinity values in the nM range for 3 members, namely BRD2-BD1 and both BRDs of BRD3, and low µM affinity to the other members ($K_d$ values between 1.5 and 3.5 µM).

So far, no molecules exhibiting binding selectivity within the BET family have been reported, probably due to the similarity of their binding pockets, both in terms of 3-dimensional structure and amino acid sequence. A recent classification of the BRD family pointed out that the CREBBP and EP300 BRDs had binding site amino acid signatures in common with the BET bromodomains. Indeed, the compound of formula (4) showed ~3.5 µM binding affinity to these two other BRDs. This result is remarkable, as only a few small molecules displaying significant binding to those proteins have been described so far. In the case of CREBBP, the compound ischemin ($K_d$=19 µM) was found to inhibit its association with p53, further blocking apoptosis in cardiomyocytes.

Antiproliferative Activity Against Leukaemia Cells

BRD4 is a validated therapeutic target in NUT midline carcinoma and in acute myeloid and MLL-fusion leukaemia. The proliferation inhibition potential of the virtual screening hits in HL-60 and HeLa cell lines for the compound of formula (4) was assessed. The compound of formula (4) exhibited a $GI_{50}$ value between 5 and 20 µM in HL-60 cells and no antiproliferative activity against HeLa at a high concentration of 50 µM.

The antiproliferative potential of the compound of formula (4) was also assessed by means of the NCI-60 DTP Human Tumour Cell Line Screen. This assay consisted of 56 cell lines representing 9 different cancer types. The results are summarized in FIG. 2.

Figure 2:
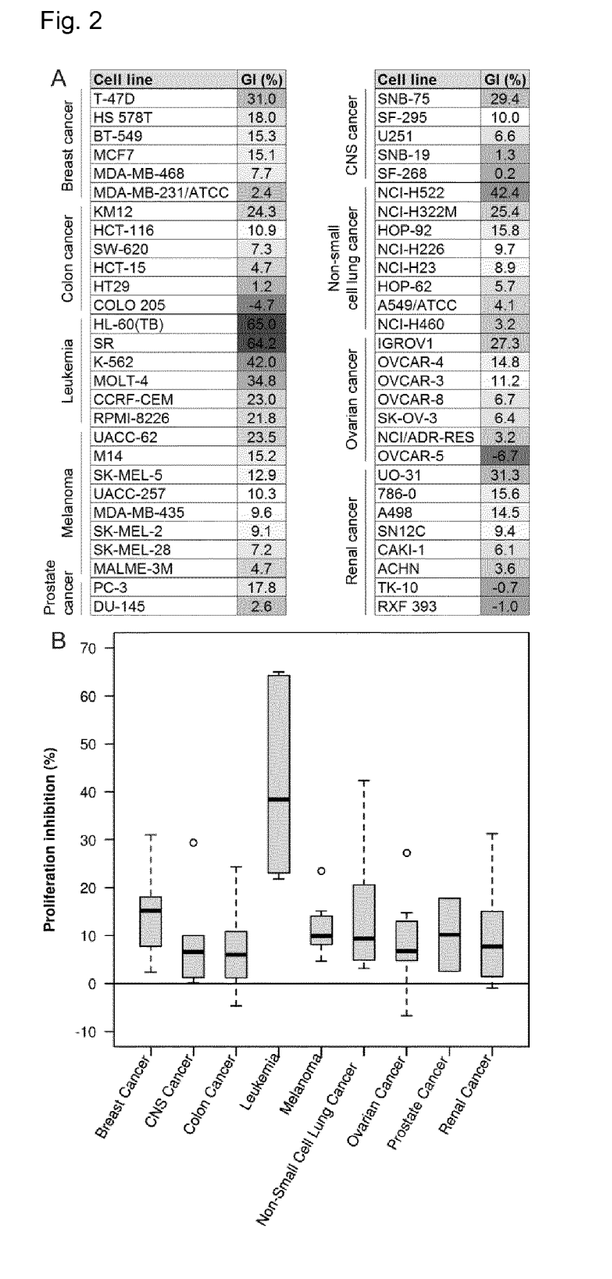
FIG. 2 summarizes results for an NCI-GO DTP human tumour cell line screen, (A) growth inhibition (GI, %), (B) proliferation inhibition (%).

FIG. 2 shows a NCI-60 DTP Human Tumour Cell Line Screen. Part A shows the growth inhibition (GI, %) observed after incubation of each cell line with the compound of formula (4) at a concentration of 10 µM. Part B shows a box plot representation of the proliferation inhibition (%) of the cell lines grouped by cancer type. The compound of formula (4) showed potent and selective activity against the leukaemia cell lines represented in the assay. Indeed, the most sensitive cells were HL-60(TB) and SR, from the leukaemia panel, whereas the most resistant were OVCAR-5 and COLO 205, from ovarian and colon cancer respectively. The Cell Line Screen results indicate that the compound of formula (4) selectively inhibits the proliferation of leukaemia cells.

Three descriptors to determine whether the compounds for use in accordance with the present invention have desirable drug-like properties were calculated. Quantitative estimate of drug-likeness (QED) is a recently developed measure of drug-likeness based on the concept of desirability of physicochemical descriptors present in drugs (Bickerton G R, Paolini G V, Besnard J, Muresan S, & Hopkins A L (2012), Quantifying the chemical beauty of drugs, *Nature chemistry* 4(2):90-98). Ligand efficiency indexes provide a measure of how efficiently a ligand binds to a biomolecule with respect to the magnitude of a physical property of the compound. Thus, we have computed the ligand efficiency in terms of number of heavy atoms (LE) and lipophilicity per unit of potency (LLE) (Hopkins A L G C, Alex A. (2004), Ligand efficiency: a useful metric for lead selection, *Drug discovery today* 9(10):430-431; Leeson P D & Springthorpe B (2007), The influence of drug-like concepts on decision-making in medicinal chemistry, *Nature reviews, Drug discovery* 6(11):881-890)

Table 1 summarizes the drug-likeness analysis for the compound of formula (4) and for the compound of formula (3) with $R_5$ being methyl, and the reference compounds, JQ1 and I-BET. QED scores indicate that the four molecules are drug-beauty, with the compound of formula (4) and JQ1 having the lowest values in the range of 0.4. LE has proven useful in the estimation of the potency of a compound to disrupt a protein-protein complex (Wells J A & McClendon C L (2007), Reaching for high-hanging fruit in drug discovery at protein-protein interfaces, *Nature* 450(7172):1001-1009). It could be shown that potent inhibitors had LE values above 0.24. Interestingly, the compound of formula (4) has a LE of 0.31, similar to that of JQ1 and I-BET. The compound of formula (3) with $R_5$ being methyl, as a representative of the new 4-acyl pyrrole BET family inhibitors, displayed the highest ligand efficiency indexes among the studied compounds, with an LE value of 0.43 and LLE of 3.7. The analysis of the drug-likeness and physicochemical properties of the compound of formula (4) and the compound of formula (3) with $R_5$ being methyl indicate that the 4-acyl pyrrole moiety is an interesting scaffold for the development of molecules binding to the BET bromodomains.

TABLE 1

Summary of drug-likeness and ligand efficiency index parameters computed for compound of formula (4), compound of formula (3), JQ1, and I-BET. $pK_d$, quantitative estimate of drug-likeness (QED), ligand efficiency (LE, calculated as 1.37($pK_d$/number of heavy atoms), kcal · mol⁻¹ · heavy atom⁻¹), and ligand-lipophilicity efficiency (LLE, calculated as $pK_d$ - clog$P_{o/w}$) are shown

|  | $pK_d$ | QED | LE | LLE |
| --- | --- | --- | --- | --- |
| Compound of formula (4) | 6.5 | 0.41 | 0.31 | 2.8 |
| Compound of formula (3) | 4.7 | 0.73 | 0.43 | 3.7 |
| JQ1 | 7.6 | 0.44 | 0.34 | 3.5 |
| I-BET | 7.3 | 0.65 | 0.33 | 3.9 |

Toxicity Screening of Compound (4)

A single dose of the compound of formula (4) at 2000 mg/kg did not induce any signs of toxicity. The value of LD50 of the substance for mice (male and female) is higher than 2000 mg/kg of body weight. All studied organs and tissues had the structure characteristics and relative body weights for normal animals.

EXAMPLE 2

Affinity Profiling for Compound of Formula (3) with $R_5$ being Methyl in the Human Bromodomain Family Bromodomain profiling was carried out on the basis of BROMOscan™, which is a leading platform for identifying small molecule bromodomain inhibitors. BROMOscan™ employs a proprietary ligand binding site-directed competition assay to quantitatively measure interactions between test compounds and bromodomains. The reliable assay panel is suitable for high-throughput screening and delivers quantitative ligand binding data.

Compounds that bind the bromodomain prevent its binding to the immobilized ligand thus reducing the amount of protein captured. Conversely, molecules that do not bind the bromodomain have no effect on the amount of protein captured. Hits are identified by measuring the amount of bromodomain captured in test versus control samples.

Protocol Description

Bromodomain assays: T7 phage strains displaying bromodomains were grown in parallel in 24-well blocks in an *E. coli* host derived from the BL21 strain. *E. coli* were grown to log-phase and infected with T7 phage from a frozen stock (multiplicity of infection=0.4) and incubated with shaking at 32° C. until lysis (90-150 minutes). The lysates were centrifuged (5,000×g) and filtered (0.2 µm) to remove cell debris. Streptavidin-coated magnetic beads were treated with biotinylated small molecule or acetylated peptide ligands for 30 minutes at room temperature to generate affinity resins for bromodomain assays. The bound beads were blocked with excess biotin and washed with blocking buffer (SeaBlock (Pierce), 1% BSA, 0.05% Tween 20, 1 mM DTT) to remove unbound ligand and to reduce non-specific phage binding. Binding reactions were assembled by combining bromodomains, bound affinity beads, and test compounds in 1× binding buffer (16% SeaBlock, 0.32×PBS, 0.02% BSA, 0.04% Tween 20, 0.004% Sodium azide, 7.9 mM DTT). Test compounds were prepared as 1000× stocks in 100% DMSO and subsequently diluted 1:25 in mono ethylene glycol (MEG). The compounds were then diluted directly into the assays such that the final concentrations of DMSO and MEG were 0.1% and 2.4%, respectively. All reactions were performed in polypropylene 384-well plates in a final volume of 0.02 ml. The assay plates were incubated at room temperature with shaking for 1 hour and the affinity beads were washed with wash buffer (1×PBS, 0.05% Tween 20). The beads were then re-suspended in elution buffer (1×PBS, 0.05% Tween 20, 2 µM non-biotinylated affinity ligand) and incubated at room temperature with shaking for 30 minutes. The bromodomain concentration in the eluates was measured by qPCR.

The compounds were screened at a concentration of 50 000 nM and results for primary screen binding are reported as % of control where lower numbers indicate a stronger binding (there is stronger inhibition of the control binding).

The % Ctrl values were determined as follows:

% Ctrl=[(test compound signal-positive control signal)/(negative control signal-positive control signal)]×100 where test compound was the compound of formula (3) with $R_5$ being methyl, negative control was DMSO (100% Ctrl) and positive control was the control compound (0% Ctrl)

Table 2 shows the results for a group of 24 bromodomains:

TABLE 2

| Target bromodomain | % Ctrl @50 000 nM |
|---|---|
| ATAD2A | 98 |
| ATAD2B | 79 |
| BAZ2A | 28 |
| BAZ2B | 23 |
| BRD1 | 19 |
| BRD2(1) | 8.4 |
| BRD2(2) | 11 |
| BRD3(1) | 10 |
| BRD3(2) | 5.2 |
| BRD4(1) | 12 |
| BRD4(2) | 8.6 |
| BRDT(1) | 19 |
| BRDT(2) | 26 |
| BRPF1 | 0 |
| BRPF3 | 44 |
| CREBBP | 21 |
| EP300 | 32 |
| FALZ | 21 |
| PBRM1(2) | 75 |
| TAF1(2) | 45 |
| TAF1L(2) | 48 |
| TRIM24(PHD, Bromo) | 86 |
| TRIM33(PHD, Bromo) | 100 |
| WDR9(2) | 39 |

The results show that the compounds showed very good to average binding affinity to 15 bromodomains (less than 35% Ctrl).

Figure 3:
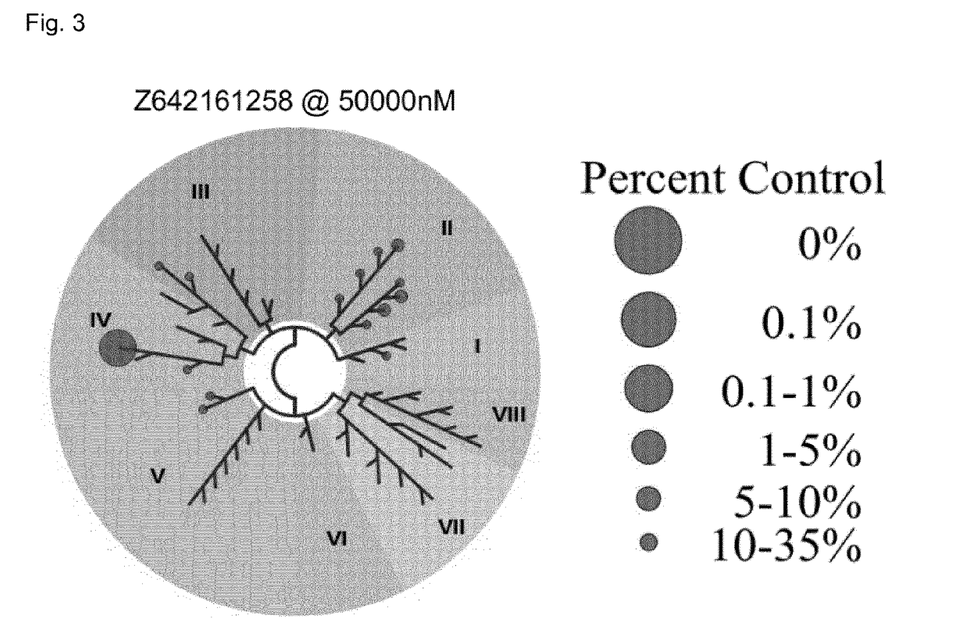
FIG. 3 shows BROMOscan™ for a compound (3).

FIG. 3 shows BROMOscan™ results for Compound (3) with $R_5$=Me. This figure complements the data shown in Table 2. Family II represents the BET bromodomain family, and Family IV highlights the potent inhibition of BRPF1

For 7 bromodomains other than the bromodomains from the BET family dissociation constants $K_d$ were determined and the results are given in Table 3.

TABLE 3

| Target bromodomain | $K_d$ (nM) |
|---|---|
| BAZ2A | 28000 |
| BAZ2B | 16000 |
| BRD1 | 12000 |
| BRPF1 | 2400 |
| CREBBP | 36000 |
| EP300 | >50000 |
| FALZ | >50000 |

The results indicate that the compound of formula (3) with $R_5$ being methyl provides a promising starting point for the development of novel potent bromodomain inhibitors.

The invention claimed is:

1. A method of treatment comprising administering to a subject in need thereof and having a disease or condition selected from the group consisting of chronic autoimmune or inflammatory condition, cancer, viral diseases, obesity, kidney malfunction or for the inhibition of proliferation of leukemia cells or as a male contraceptive a therapeutically effective amount of a bromodomain inhibitor of formula (3)

(3)

or a pharmaceutically acceptable salt thereof
wherein $R_5$ is selected from hydrogen or a substituted or unsubstituted $C_3$-$C_{14}$ aryl group, which may be attached directly or through a spacer of a $C_1$-$C_8$ alkylene group, which $C_3$-$C_{14}$ aryl group may be unsubstituted or substituted with a substituent selected from halogen, alkyl, alkoxy, cyano, alkenyl, alkynyl, arylalkyl, aryl and heteroaryl groups.

2. The method of treatment in accordance with claim 1 wherein $R_5$ is a substituted phenyl group, which may be attached directly or through a spacer of a $C_1$-$C_8$ alkylene group.

3. The method of treatment in accordance with claim 2 wherein $R_5$ is the substituent of formula (2)

(2)

wherein $R_9$ is halogen, OH, SH, $SR_6$, cyano, thiocyanato, isothiocyanato, $NR_6R_7$, a $C_1$-$C_8$ alkyl group, a $C_2$-$C_8$ alkylene group, a $C_2$-$C_8$ alkynyl group or a $C_1$ to $C_8$ alkoxy group,
wherein $R_6$ and $R_7$, which may be the same or different, are hydrogen or a $C_1$ to $C_8$ alkyl group, and n is an integer of from 0 to 4, and $R_{10}$ and $R_{11}$, which may be the same or different, are hydrogen, a $C_1$-$C_6$ alkyl group or a substituted or unsubstituted $C_3$-$C_{14}$ cycloalkyl group, heterocycloalkyl, aryl or heteroaryl group, or wherein $R_{10}$ and $R_{11}$ may form together a cyclocarbyl, heterocyclocarbyl, aryl or heteroaryl ring, each with 3 to 14 carbon atoms.

4. A method of treatment in accordance with claim 1, wherein the compound is represented by formula (4) or a pharmaceutically acceptable salt thereof (4)

5. The method of treatment according to claim 1 wherein the disease or condition is a chronic autoimmune or inflammatory condition, cancer or a viral disease.

6. The method of treatment in accordance with claim 1 for the inhibition of proliferation of leukaemia cells.

7. The method of treatment according to claim 1 wherein the disease or condition is obesity.

8. The method of treatment according to claim 1 wherein the disease or condition is a kidney malfunction.

9. The method of treatment according to claim 1 as a male contraceptive.

10. A method of treatment comprising administering to a subject in need thereof and having a disease or condition selected from the group consisting of chronic autoimmune or inflammatory condition, cancer, viral diseases, obesity, kidney malfunction or for the inhibition of proliferation of leukemia cells or as a male contraceptive, a therapeutically effective amount of a pharmaceutical composition comprising at least one compound of formula (3), in accordance with claim 1 or a pharmaceutically acceptable salt thereof and one or more pharmaceutically acceptable carriers, diluents or excipients.

11. The method of treatment in accordance with claim 1 wherein Z is C.

12. The method of treatment in accordance with claim 3 wherein n is an integer from 1 to 3.

13. The method of treatment in accordance with claim 1 wherein $R_5$ is $C_1$-$C_8$-alkyl.

14. The method of treatment in accordance with claim 1 wherein $R_5$ is methyl.

15. A method of treatment comprising administering to a subject in need thereof and having a disease or condition selected from the group consisting of chronic autoimmune or inflammatory condition, cancer, viral diseases, obesity, kidney malfunction or for the inhibition of proliferation of leukemia cells or as a male contraceptive, a therapeutically effective amount of a combination pharmaceutical product comprising at least one compound of formula (3) in accordance with claim 1 or a pharmaceutically acceptable salt thereof and one or more pharmaceutically acceptable carriers, diluents or excipients together with one or more other pharmaceutically active ingredients.

* * * * *

UNITED STATES PATENT AND TRADEMARK OFFICE
CERTIFICATE OF CORRECTION

PATENT NO. : 10,435,364 B2  
APPLICATION NO. : 14/784620  
DATED : October 8, 2019  
INVENTOR(S) : Stefan Guenther et al.

It is certified that error appears in the above-identified patent and that said Letters Patent is hereby corrected as shown below:

In the Claims

In Claim 3, at Column 1, Lines 46-47, replace the phrase "a C1-C6 alkyl group" with the phrase "a C1-C8 alkyl group".

Signed and Sealed this  
Twenty-sixth Day of November, 2019

Andrei Iancu  
*Director of the United States Patent and Trademark Office*